United States Patent
Reif et al.

(10) Patent No.: US 6,951,613 B2
(45) Date of Patent: Oct. 4, 2005

(54) GENETIC VACCINATION DEVICE AND PROCESS FOR FORMING AN INJECTION THEREFOR

(75) Inventors: Oscar-Werner Reif, Hannover (DE); Thomas Scheper, Hannover (DE); Karl Friehs, Sehnde (DE)

(73) Assignee: Sartorius AG, Goettingen (DE)

( * ) Notice: Subject to any disclaimer, the term of this patent is extended or adjusted under 35 U.S.C. 154(b) by 0 days.

(21) Appl. No.: 10/264,491

(22) Filed: Oct. 4, 2002

(65) Prior Publication Data

US 2003/0068354 A1 Apr. 10, 2003

(30) Foreign Application Priority Data

Oct. 5, 2001 (DE) ......................................... 101 49 251

(51) Int. Cl.⁷ .............................................. B01D 29/60
(52) U.S. Cl. ................... 210/416.1; 210/435; 210/483; 210/490; 210/502.1; 424/423; 514/44; 604/187
(58) Field of Search ............................. 210/416.1, 435, 210/483, 490, 502.1; 424/423; 514/44; 604/187

(56) References Cited

U.S. PATENT DOCUMENTS

| 4,366,822 A | * | 1/1983 | Altshuler ..................... 600/566 |
| 5,000,854 A | * | 3/1991 | Yang ........................... 210/638 |
| 6,117,394 A | * | 9/2000 | Smith .......................... 422/100 |
| 6,262,172 B1 | * | 7/2001 | Yu et al. ..................... 525/54.2 |
| 6,274,726 B1 | * | 8/2001 | Laugharn et al. .......... 536/25.4 |

* cited by examiner

*Primary Examiner*—W. L. Walker
*Assistant Examiner*—K S Menon
(74) *Attorney, Agent, or Firm*—Chernoff, Vilhauer, McClung & Stenzel, LLP

(57) ABSTRACT

There is disclosed a genetic vaccination device and a process for forming an injection solution therefor, the device comprising a syringe and canula coupled to a membrane adsorber having genetic material adsorbed thereon, and the process comprising eluting the genetic material from the membrane adsorber so as to form an injection solution containing the genetic material.

11 Claims, 1 Drawing Sheet

GENETIC VACCINATION DEVICE AND PROCESS FOR FORMING AN INJECTION THEREFOR

Pursuant to 35 USC §119, the priority of DE 101 49 251.0 filed Oct. 5, 2001 is claimed.

BACKGROUND OF THE INVENTION

Genetic immunization, also known as DNA or nucleic acid vaccination, is an immunization method whereby, in contrast to conventional immunization, antigen-coded nucleic acids rather than antigens are injected and the immunization reaction then acts counter to the protein which is generated. Such vaccination with nucleic acids is typically conducted in humans or in animals by injection or by ballistic transmission, i.e., by a so-called "gene-gun." Pure or so-called "naked" DNA is administered generally in the form of plasmids. The DNA migrates through unknown pathways into the cells of the patient's body, thereby penetrating to the cores of the cells. In the core, the DNA transcribes (constructs a messenger RNA molecule using the DNA molecule as a template, resulting in transfer of the genetic information to the RNA) and the resulting messenger RNA (mRNA) subsequently translates (forms a protein molecule at a ribosomal site of protein synthesis from information contained in the mRNA) into the cytoplasm, whereupon the protein generated thereby releases the immunological response. In the case of humans, very frequently the promoter of the human cytomegalovirus (CMV) is employed as an adjuvant or control element for various DNA types. There are, however, other useful adjuvants, both for humans and animals, such as SV40. In the case of RNA types, ribosomes may be also used as adjuvants.

The genes necessary for immune response, which are coded for the significant proteins, can be prepared in sufficient quantities for use on plasmids in, for example, microorganisms such as $E.\ coli$. With the aid of the plasmid technology, it is possible to transfer only the genes, resulting in an effective, side effect-free immune response. Plasmids themselves can also be multiplied relatively simply in $E.\ coli$. The quality demands on the genetic materials for injection include homogeneity and freedom from endotoxins in addition to the customary requirements for purity and freedom from proteins.

For genetic vaccination, the injection is conventionally an aqueous solution of the active agent packaged in an ampoule, from which the injection is withdrawn into a syringe and administered. A major drawback of such a vaccination is that nucleic acids are seldom stable in aqueous solutions. Accordingly, for shipment and storage, substantial preventive measures must be taken. A second drawback is that warm climates drastically reduce the effectiveness of such injection solutions.

Accordingly it is a primary goal of the present invention to provide a device for genetic vaccination that permits the transport and storage of the DNA vaccine simply and that avoids the aforementioned drawbacks of the prior art, and to provide a process of forming a genetic vaccine that is similarly free of the prior art drawbacks.

BRIEF SUMMARY OF THE INVENTION

According to the present invention, a membrane adsorber cartridge containing at least one membrane adsorber onto which genetic material is bound is interposed between a syringe and a canula and in fluid communication with both. An elution solution can be passed through the membrane adsorber, which elutes the genetic material, thereby forming the desired injection solution.

Because the genetic material is bound to the membrane, it can be lyophilized, so that it can be stored in the dry state. This feature permits world-wide shipments of key genetic vaccine components without any stability or degradation problems, even in cases of difficult climatic conditions. The active genetic materials bound onto the membrane adsorber are so entirely free from deterioration that they can be sent by post or other conventional shipping methods. In addition, since the genetic material-containing membrane adsorber can be shipped without liquid, the packaging therefor is lightweight. Even multi-year storage of the membrane adsorber carrying the bound active genetic material is possible without any substantial loss in its potency. The invention also makes it possible to vaccinate against a plurality of antigens with a single vaccination.

DETAILED DESCRIPTION OF PREFERRED EMBODIMENTS

Figure 1:
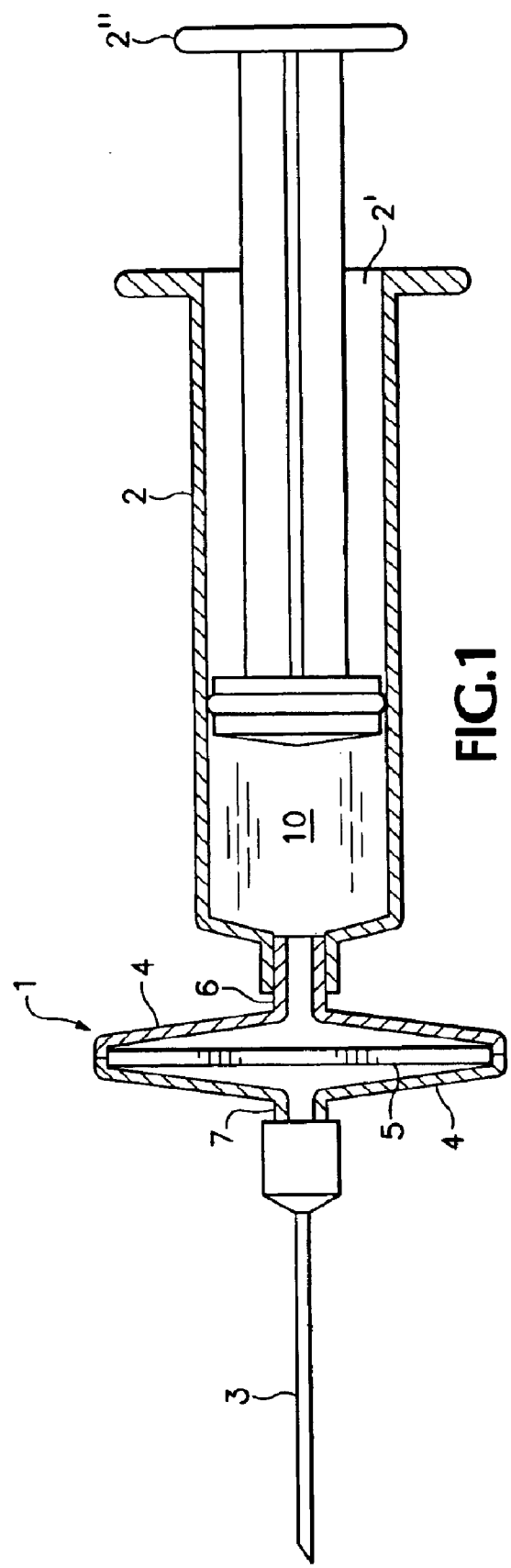
FIG. 1 is a sectional schematic of an exemplary device of the invention.

Referring to the drawing, there is shown in FIG. 1 a membrane adsorber cartridge 1, coupled to a syringe 2 and to a canula 3 and situated between syringe 2 and canula 3. Syringe 2 consists of syringe barrel 2' and plunger 2". The barrel contains an elution fluid 10. Membrane adsorber cartridge 1 consists of a two-part housing 4 containing a membrane adsorber 5, which has one or more active agents adsorbed thereon. The membrane adsorber is preferably an anion exchange membrane, for example, Sartobind® from Sartorius AG of Göttingen, Germany. Housing 4 incorporates a syringe fitting 6 adapted to couple fluid-tight with syringe barrel 2', as well as a canula fitting 7 proximal to and adapted to couple fluid-tight with canula 3.

The active material is preferably in the form of DNA plasmids adsorbed onto the membrane adsorber 5. To form an injection solution, syringe 2 is filled with an elution fluid 10 and the membrane adsorber cartridge 1 is coupled to syringe 2 and injection canula 3. Elution solution 10 is forced through syringe barrel 2' and membrane adsorber 5 by plunger 2", so that the active agent on membrane adsorber 5 is eluted and the eluate, which now forms the injection solution carrying the active agent, is injected into, for instance, a muscle or a vein of the patient by canula 9.

The use of membrane adsorbers in the present invention makes possible a simple, well-defined loading of genetic vaccination material, permitting easy validation. Furthermore, the membrane adsorbers form an integrated endotoxin filter that is easily sterilized. Multiple loading with a plurality of DNA vaccines is also possible. Thus, an inoculation for Hoof and Mouth Disease (HMD) with an added tracer vaccine to form a easily detectable antibody can be carried out without difficulty.

In another preferred embodiment of the invention, an adjuvant can be supplied with the active material which may be superimposed as a DNA sequence on the antigen-coded nucleic acids. It is also possible to include a second membrane adsorber in the membrane adsorber cartridge, onto which another additive or adjuvant has been bound.

Certain relatively short DNA-base sequences may serve as adjuvants. Such sequences allow themselves to be superimposed on the antigen-coded nucleic acids, so that even a portion of the DNA molecule acts as the adjuvant, allowing a substantial simplification and reduction of side-effects such as allergys and autoimmune disorder symptoms that are often triggered by conventional adjuvants.

Because the membrane adsorber cartridge can be coupled by conventional fittings to needles and syringes, it can be applied in a multitude of applications. Conventional inexpensive and easily prepared solutions such as aqueous saline solutions can be used for the elution solution. In addition, the invention permits the injection solution for genetic vaccination to be prepared immediately prior to the injection.

Genetic vaccinations can be used, for example, in cases of hepatitis B, HIV/AIDS, mutant tuberculosis and in the treatment of cancer by stimulating the immune system to destroy cancer cells. Another possible application is in the field of veterinary vaccines, for example, in the treatment of Bovine Spongiform Encephalitis (BSE) and HMD, as noted above.

The terms and expressions which have been employed in the foregoing specification are used therein as terms of description and not of limitation, and there is no intention in the use of such terms and expressions of excluding equivalents of the features shown and described or portions thereof, it being recognized that the scope of the claims which follow.

What is claimed is:

1. A device for the injection of material comprising a syringe and a canula having at least one membrane adsorber cartridge between and in fluid communication with said syringe and said canula, said at least one membrane adsorber cartridge comprising a housing containing an anion exchange membrane adsorber that has genetic material adsorbed thereon and is capable of reversibly binding nucleic acids.

2. The device of claim 1 wherein said genetic material is coded DNA.

3. The device of claim 2 wherein said genetic material is selected from the group consisting of plasmids, plasmid derivatives and linear DNA.

4. The device of claim 1 wherein said genetic material is selected from the group consisting of RNA, c-DNA and m-RNA.

5. The device of claim 4 including at least one additive adsorbed on said membrane adsorber.

6. The device of claim 4 wherein said genetic material is enhanced with at least one adjuvant.

7. The device of claim 6 wherein said adjuvant is a DNA sequence.

8. The device of claim 7 wherein said DNA sequence is superimposed on antigen-coded plasmids.

9. The device of claim 1 wherein said membrane adsorber has endotoxins adsorbed thereon so as to form an endotoxin filter.

10. The device of claim 1 including a second membrane adsorber in said cartridge having at least one adjuvant bonded thereto.

11. The device of claim 1 or 10 including a sterile filter disposed downstream of said canula.

\* \* \* \* \*

UNITED STATES PATENT AND TRADEMARK OFFICE
CERTIFICATE OF CORRECTION

PATENT NO. : 6,951,613 B2
DATED : October 4, 2005
INVENTOR(S) : Reif et al.

It is certified that error appears in the above-identified patent and that said Letters Patent is hereby corrected as shown below:

Title page,
Item [75], Inventors, after "Karl Freihs, Sehnde(DE)" add -- Heribert Offermanns, Hanau (DE) --.

Signed and Sealed this

Tenth Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,951,613 B2  
APPLICATION NO. : 10/264491  
DATED : October 4, 2005  
INVENTOR(S) : Reif et al.

Page 1 of 1

It is certified that error appears in the above-identified patent and that said Letters Patent is hereby corrected as shown below:

<u>Title page,</u>
Item [75], Inventors, after "Karl Friehs, Sehnde(DE)" add -- Heribert Offermanns, Hanau (DE) --.

This certificate supersedes Certificate of Correction issued January 10, 2006.

Signed and Sealed this

Twenty-eighth Day of November, 2006

JON W. DUDAS  
*Director of the United States Patent and Trademark Office*